United States Patent [19]

Vaughn

[11] Patent Number: 4,924,481
[45] Date of Patent: May 8, 1990

[54] RADIOGRAPHIC INSPECTION OF TUBE WELDS IN PANEL WALLS

[75] Inventor: Henry P. Vaughn, Canal Fulton, Ohio

[73] Assignee: The Babcock & Wilcox Company, New Orleans, La.

[21] Appl. No.: 374,728

[22] Filed: Jul. 3, 1989

[51] Int. Cl.⁵ ............................................. G01B 15/06
[52] U.S. Cl. .......................................... 378/59; 378/51
[58] Field of Search ..................................... 378/58, 59

[56] References Cited

U.S. PATENT DOCUMENTS 3,958,120  5/1976  Ward ....................................... 378/59
4,567,012  1/1986  Radcliff ................................. 378/59

OTHER PUBLICATIONS

1986 ASME Code, Section V, Article 2, "Radiographic Examination".
R. Halmshaw, Non-Destructive Testing, Copyrighted 1987, pp. 90 and 91.

Primary Examiner—Craig E. Church
Attorney, Agent, or Firm—R. J. Edwards; Michael L. Hoelter

[57] ABSTRACT

A method of inspecting tube welds in tubular membrane panel walls whereby a radiation source if placed intermediate adjacent tube welds with radiographic film positioned along the far wall of each adjacent tube thereby covering the far wall critical area of each tube weld. Simultaneously each radiographic film is exposed to an intermediate radiation source thereby creating an actual size image of each tube weld with both images totaling or equaling at least one full weld being radiographed per exposure.

10 Claims, 3 Drawing Sheets

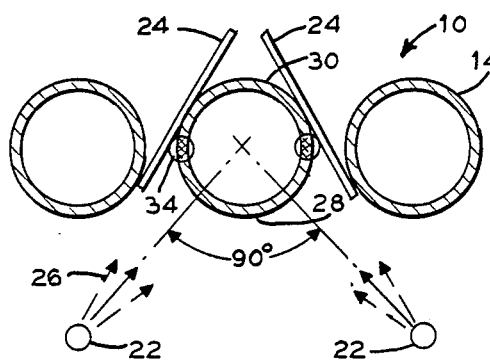
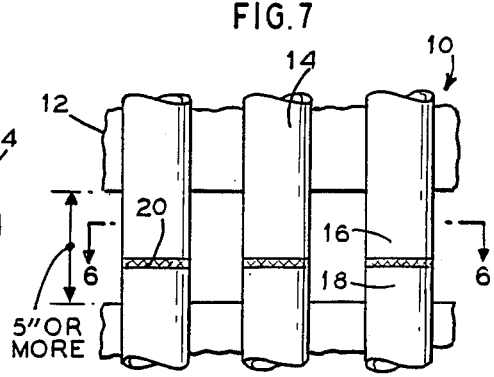
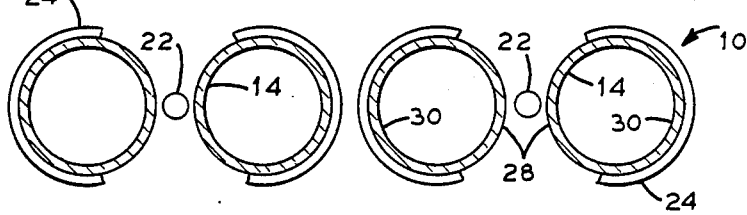
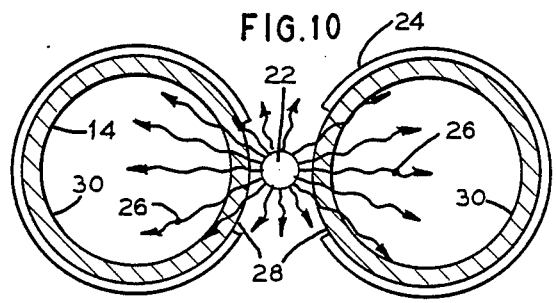
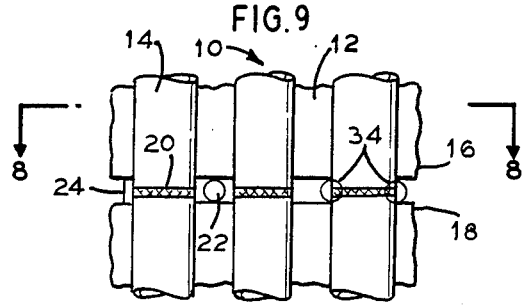

RADIOGRAPHIC INSPECTION OF TUBE WELDS IN PANEL WALLS

FIELD OF THE INVENTION

This invention pertains to tubular membrane panel walls and more particularly to the radiographic inspection of the tube welds joining two such panel walls together.

BACKGROUND OF THE INVENTION

It is now very common to construct steam generating facilities having a furnace constructed of prefabricated tubular membrane panel walls. These panel walls serve as a heat-absorbing surface and also provide a gas tight flow circuit for the generation of steam.

During the construction of the furnace, several panel wall units must be welded together to create the elongated furnace enclosure. Normally the tubes of these panel wall units are welded end-to-end, but sometimes a mid-region of a tube must be cut and re-welded for proper installation. No matter where the weld occurs, for safety's sake, the tube weld must be inspected to insure its compliance with a variety of guidelines, specifications, and codes. In particular, the critical portion of each tube weld (where the tube and the adjacent membrane bar are joined) must be inspected to prevent any possible failure under pressure.

The preferred inspection technique is radiography which creates an image of a number of tube welds simultaneously on radiographic film. This radiographic technique places the source of radiation some distance from the front of the panel wall with X-ray film being placed or taped on the other side of the panel wall. The radiation source is also vertically offset from the tube weld by about 15 to 20 degrees in order to separate the tube weld image of the near wall from that of the far wall on the X-ray film. Additionally, this method requires no cutting or removal of the membrane between adjacent tubes. Unfortunately, this technique cannot provide a clear image of the critical area of the tube weld because on the film the front critical area is superimposed over the back critical area, thereby distorting both images.

An improvement of this method is one where the source is not only vertically offset from the tube weld but is also offset to the right or left of the tube weld. Accordingly, the radiographic film must also be moved from its position adjacent to the back of the tube welds to a position along the side of each tube weld so as to remain generally perpendicular to the rays emanating from the offset source. This new position of the film necessitates the removal of a segment of the membrane bar between adjacent tubes. The additional cost incurred to remove and replace this membrane bar segment is considered well spent if the critical area of the tube weld can be inspected. Unfortunately, this is not the case because first, the offset of the source to the right or left cannot be too great or else the adjacent tube will block or interfere with the x-rays emanating from the source. Second, and precisely because of this lack of clearance with adjacent tubes, the front critical area of the tube weld will, on the film, still be superimposed over that of the back critical area of the tube weld. Another drawback is the fact that with this method, two 'shots' or views of each tube weld are required (one for the left critical area and one for the right) to obtain a full view of the tube weld; thus costs are six fold. However, this second method does provide better coverage of the critical area than does the first method; unfortunately, it is still a distorted view of the critical area and its coverage is still less than 100%.

It is thus an object of this invention to disclose an inspection system whereby 100% coverage of the tube weld is achieved including the critical area. It is also an object of this invention to describe a system whereby only one radiographic image need be taken to view a full tube weld. A further object is to eliminate any distortion of the image of the tube weld on the film. Another object is to provide an 'actual size' image of the tube weld to aid in its inspection and/or investigation. Still a further object is to reduce the exposure time and the emissivity of the source required for each radiographic image thereby increasing the margin of safety for the personnel using such radioactive material. Yet another object of this invention is to reduce the time required to set up and complete each radiograph shot. These and other objects and advantages of the invention will become apparent upon further investigation.

SUMMARY OF THE INVENTION

This method of inspecting tube welds in tubular membrane panel walls comprises the steps of installing a radiation source intermediate and adjacent to a pair of tube welds in a tubular membrane panel wall. Normally, to accomplish this, a portion of the membrane bar between the adjacent tube welds must first be removed. After such installation (or before if desired), a radiation receiver, such as x-ray film, is secured around a portion of the perimeter of each tube weld. These radiation receivers are bent or curved around their respective perimeter portion in order to conform to and cover at least 50% of each tube weld plus one of the critical areas of each tube weld (a critical area being where a tube and its adjacent membrane bar are joined). Once the above are in place, the radiation receivers are exposed simultaneously to the radiation source thereby creating an image of the covered portion of each tube weld.

BRIEF DESCRIPTION OF THE DRAWINGS

FIG. 6 is a top view, with the membrane bar cut away, taken along lines 6—6 of FIG. 7 and illustrating another conventional manner of inspecting tube welds.

FIG. 7 is a front pictorial view, partially cut away, disclosing the removed membrane required for the manner of inspection depicted in FIG. 6.

FIG. 8 is a top view, with the membrane removed, taken along lines 8—8 of FIG. 9 and illustrating applicant's manner of inspecting tube welds.

FIG. 9 is a front pictorial view, partially cut away, disclosing the removed membrane required for applicant's manner of inspection depicted in FIG. 8.

FIG. 10 is a top pictorial view, partially cut away, illustrating in greater detail applicant's manner of inspection depicted in FIG. 8.

DETAILED DESCRIPTION OF THE INVENTION

Figure 1:
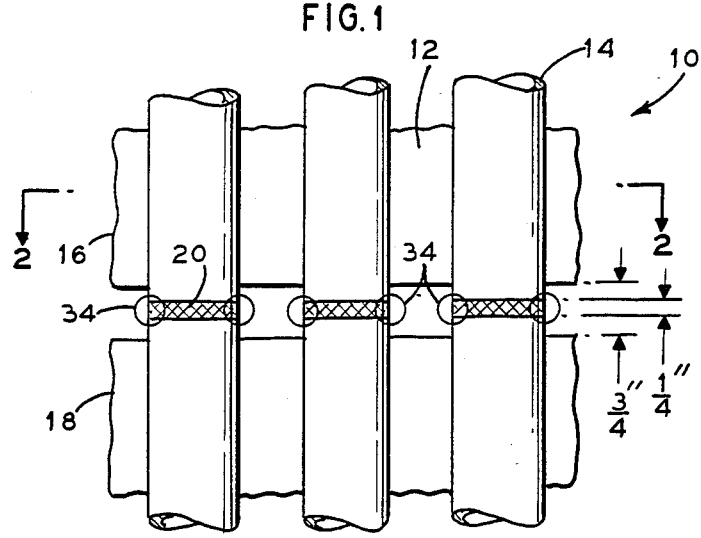
FIG. 1 is a front pictorial view partially cutaway, of a conventional juncture between adjacent tubular membrane panel wall units after being welded together but before the gap between membrane bars are sealed. The critical area of the tube welds are circled.
Figure 2:
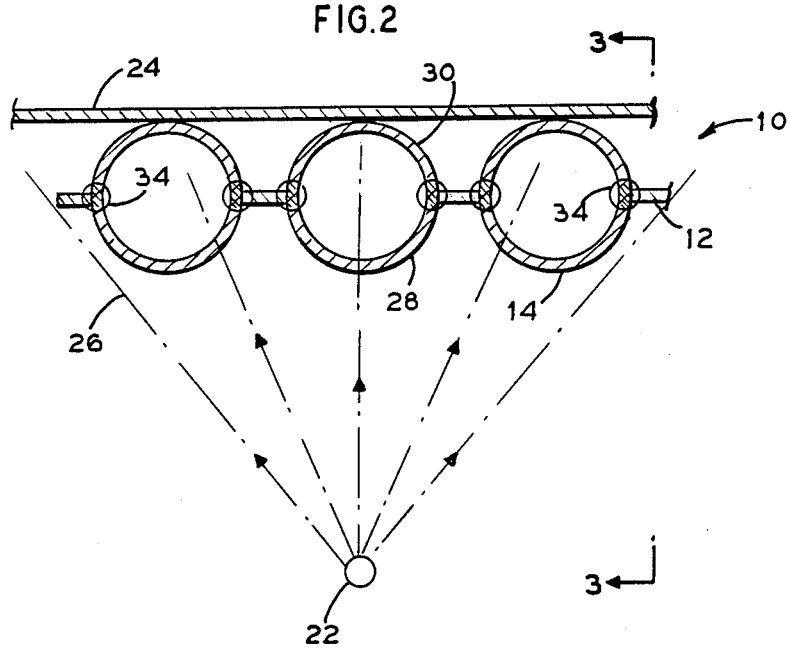
FIG. 2 is a top view, partially cutaway and taken along lines 2—2 of FIG. which illustrates one conventional manner of inspecting the tube weld. In this illustration, the critical area of the tube welds are circled.
Figure 3:
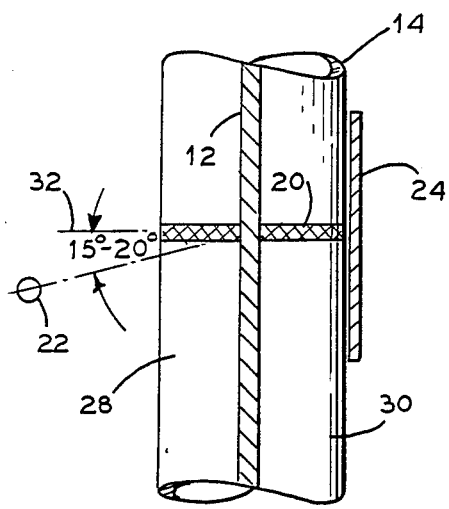
FIG. 3 is a side view, taken along lines 3—3 of FIG. 2, which illustrates the typical offset of the source from the horizontal.

Referring initially to FIG. I, there is shown tubular membrane panel wall 10 comprised of flat membrane bars 12 welded between tubes 14. Adjacent units 16 and 18 would, as shown, be welded together to create one large tubular membrane panel wall 10. During the construction of units 16 and 18, membrane bars 12 are sized so that tubes 14 extend about ¼" beyond the end of bars 12. This ¼" shortfall from adjacent ends of units 16 and 18 in addition to the approximately ¼" thickness of tube weld 20 results in a total gap of about ¾" between the ends of adjacent membrane bars 12. During construction, this gap is closed by welding to complete the wall seal in this region.

Figure 4:
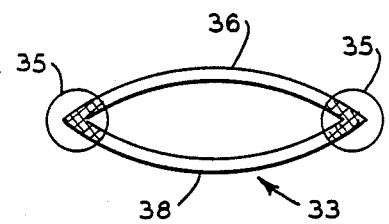
FIG. 4 is a pictorial view of the radiographic image obtained by the manner depicted in FIG. 5. The image of the critical area is emphasized.

Referring now to FIGS. 2-5, there is shown the conventional double wall imaging method of inspecting tube welds 20. As shown, radioactive source 22 is positioned some distance in front of to-be-inspected tube weld 20 with source 22 generally consisting of iridium 192 isotope. Radiographic film 24, such as x-ray film, is placed on the opposite or back side of tube weld 20 and preferably tangent to tubes 14. Rays 26 radiating from source 22 pass through tube weld 20 and impact on film 24 thereby creating an image of tube weld 20 on film 24. To prevent superimposing the image of near wall 28 of tube 14 over that of far wall 30 on film 24, source 22 is vertically offset, either above or below, from horizontal plane 32 by about 15 degrees to 20 degrees (see FIG. 3). The resulting double-wall elliptical image 33, as illustrated in FIG. 4, separates near wall 28 and far wall 30 into images 36 and 38 respectively.

Figure 5:
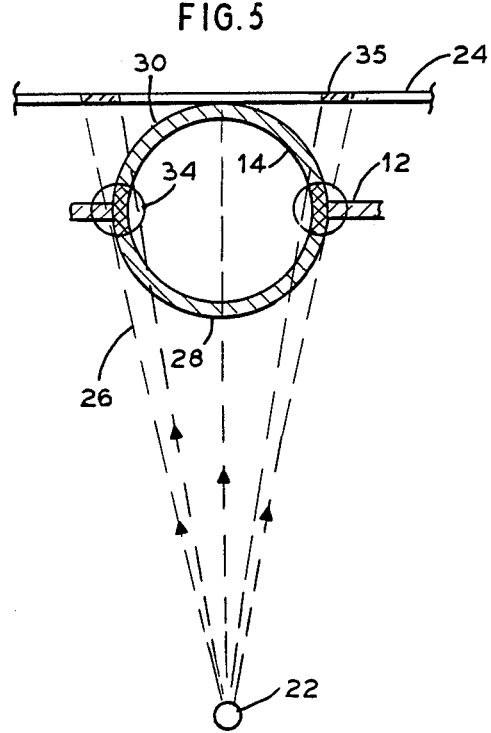
FIG. 5 is a top pictorial view partially cutaway, illustrating in greater detail the conventional manner of inspecting tube welds as shown in FIG. 2.

Of major importance is the ability to inspect the critical area 34 of tube weld 20. Critical area 34 is that portion of tube weld 20 that is adjacent to membrane bar 12. FIG. 5 illustrates the critical area 34 of typical tube 14 and its respective image 35 on film 24. As can be seen, due to the orientation of each critical area 34 being generally parallel to rays 26, the area of image 35 of these critical areas 34 on film 24 is relatively small (being located at the apex ends of elliptical image 33 of FIG. 4). Additionally, and as further indicated in FIG. 4, image 35 of critical area 34 has its near wall image 36 superimposed over its far wall image 38. Consequently, any information contained about critical area 34 on film 24 is distorted. With this method only about 65% of tube weld 20 can be imaged.

One typical method of resolving this distortion of critical area 34 is shown by the double-wall imaging radiographic technique illustrated in FIGS. 6 and 7. As indicated, source 22 is offset to the right and then to the left of tube 14 prior to the taking of each double wall image 33.

In this method, however, two separate images 33 are needed, one with respect to each critical area 34 of each tube weld 20 thus necessitating two separate set-ups for each tube. The positioning of source 22 would be about 18 inches from film 24 and the two placements would form an angle of approximately 90 degrees. Unfortunately, however, this side-to-side relocation of source 22 cannot be too great, otherwise adjacent tubes 14 will interfere with rays 26 thereby distorting any created image 33. Additionally, a rather large segment of membrane bar 12 (approximately 5 inches in length) will need to be removed (FIG. 7) so that film 24 can be properly positioned opposite its respective source 22. As indicated in FIG. 7, the removed segment need not be centered about tube weld 20.

A film size similar to that previously used (approximately 4½") is required because of the magnification of tube weld image 33 on film 24 due to outwardly radiating rays 26. The only portion of the image 33 of tube weld 20 that is actual size is that portion of film 24 tangent to tube weld 20. The critical area 34 of tube weld 20 and its related image 35 on film 24 is similar to that shown in FIG. 4 but taking into account the left and right shifting of source 22. With this method, however, the critical area image 35 on film 24 is slightly moved away from the opposite apexes. Although this method is an improvement over the earlier method, problems still remain and full coverage of tube weld 20 is still not attainable.

Applicant's contact method of radiography contemplated herein is illustrated in FIGS. 8-10. Under this method, source 22 is relocated to a position directly intermediate tube welds 20. Unlike conventional wisdom, source 22 is not offset either vertically or horizontally with respect to tube weld 20. Furthermore, film 24 is wrapped around and in contact with a portion (the far portion) of tube 14. In this fashion, and unlike the prior methods, no magnification of tube weld 20 occurs; instead, at least half of tube weld 20 is recorded on film 24 in 1 actual size ' status, including the all-important critical area 34 of far wall 30. This method also enables, as shown in FIGS. 8 and 10, the creation of two separate images of adjacent tube welds 20 from only a single exposure. Furthermore, due to the 'actual size' image created, the size of film 24 is significantly reduced, enabling film widths of only about 2½ inches to be used as compared to film widths of up to 5 inches or more required for the earlier methods due to the magnification of tube weld 20 and the vertical offsetting of source 22.

As contemplated, with this method, the construction of units 16 and 18 of tubular membrane panel wall 10 involves membrane bars 12 that are either cut back an additional inch or so on each end or are manufactured an inch or so shorter on each end. This would result in a gap between adjoining ends of membrane bars 12 of only about 2½ inches. Consequently, a significantly smaller opening (less than half) is created which would need back field welding for closing thereby reducing costs.

Film 24 would be curved or bent to fit around and contact the distant or far critical area 34 of each adjacent tube weld 20. With this arrangement and as indicated in the figures, film 24 would be spaced from source 22 no more than approximately 1 to 1½ diameters of its respective tube weld 20. Any distance over one diameter is due to the width of membrane bar 12 and/or the thickness of tube weld 20. Normally, film 24 would surround at least half (FIG. 8) of each tube weld 20. Thus, for each simultaneous exposure, at least 360 degrees of tube weld 20 is recorded resulting in 100% actual imaging of tube weld 20.

As better illustrated in FIG. 10, approximately half of each tube weld 20 can be recorded as "actual size" because rays 26 pass directly through the tube weld 20 along far wall 30 before impacting on film 24. Because source 22 is in such close contact with the critical area region adjacent near walls 28 and because it is positioned so closely between the tube welds themselves, no image of this region will appear on film 24. Instead, source 22 and this region will become vertically undistinguishable and will be recorded on film 24 as though this whole area adjacent tube welds 20 is the radiating source.

Once the images of adjacent tube welds 20 are made, source 22 is moved over one tube 14 and placed in the gap in the next membrane bar 12. Two small strips of film 24 are then placed around these two adjacent tubes 14 to again cover at least the critical area 34 of the far tube weld 20 of each tube 14 but at least 50% of each tube weld 20. Normally, film 24 is held in place by tape or a hook and loop method of securement. After a typical exposure duration of about 30 seconds (as compared to three to six minutes with other methods) the process is relocated and duplicated at the next gap in membrane bar 12 until the entire panel wall 10 is inspected. Of course, when the end of a panel wall 10 is reached, the procedure is modified so as to obtain a full view of this last tube weld 20 in the manner described above. Normally, the weld type being inspected is a butt weld of the V groove type. The material being welded is oftentimes carbon steel but in some cases the boiler tubes may be overlaid with stainless steel.

What is claimed as Invention is:

1. A radiographic method of inspecting tube welds in tubular membrane panel walls comprising the steps of:
   (a) installing a radiation source intermediate an adjacent pair of tube welds in a tubular membrane panel wall;
   (b) securing a radiation receiver around a perimeter portion of each said tube weld, said radiation receivers closely conforming to their respective perimeter portion and covering at least one critical area of its respective tube weld, a critical area of a tube weld being that region where a tube and a membrane bar join; and,
   (c) simultaneously exposing each said radiation receiver to said radiation source thereby creating an image of said perimeter portion of each said tube weld.

2. A radiographic method of inspecting tube welds as set forth in claim 1 further comprising the step of creating an approximately actual size image of each said tube weld.

3. A radiographic method of inspecting tube welds a set forth in claim 2 further comprising the step of using radiographic film and affixing it to cover the far wall critical area of each said tube weld.

4. A radiographic method of inspecting tube welds as set forth in claim 3 further comprising the initial step of removing a segment of said membrane bar intermediate said adjacent tube welds, said removed segment being sized to permit the installation of said radiation source intermediate said adjacent tube welds.

5. A radiographic method of inspecting tube welds as set forth in claim 4 further comprising the step of securing said radiation receiver around at least half the circumference of each said tube weld.

6. A radiographic method of inspecting tube welds in tubular membrane panel walls comprising the steps of:
   (a) installing a radiation source intermediate an adjacent pair of tube welds in a tubular membrane panel wall;
   (b) securing a radiation receiver around a perimeter portion of each said tube weld, the maximum distance of said source to any region of each said radiation receiver being no more than approximately 1 to 1½ diameters of its respective tube weld; and,
   (c) simultaneously exposing each said radiation receiver to said radiation source thereby creating an image of said perimeter portion of each said tube weld.

7. A radiographic method of inspecting tube welds as set forth in claim 6 further comprising the step of creating an approximately actual size image of each said tube weld.

8. A radiographic method of inspecting tube welds as set forth in claim 7 further comprising the step of using radiographic film and affixing it to cover the far wall critical area of each said tube weld.

9. A radiographic method of inspecting tube welds as set forth in claim 8 further comprising the initial step of removing a segment of said membrane bar intermediate said adjacent tube welds, said removed segment being sized to permit the installation of said radiation source intermediate said adjacent tube welds.

10. A radiographic method of inspecting tube welds as set forth in claim 9 further comprising the step of securing said radiation receiver around at least half the circumference of each said tube weld.

* * * * *